United States Patent [19]

Patarroyo

[11] Patent Number: 4,957,738

[45] Date of Patent: * Sep. 18, 1990

[54] PROTEIN COPOLYMER MALARIA VACCINE

[76] Inventor: Manuel E. Patarroyo, P.O. Boxa 4402, Bogota, Colombia

[*] Notice: The portion of the term of this patent subsequent to Apr. 5, 2005 has been disclaimed.

[21] Appl. No.: 135,027

[22] Filed: Dec. 29, 1987

Related U.S. Application Data

[63] Continuation-in-part of Ser. No. 3,194, Jan. 14, 1987, Pat. No. 4,735,799.

[51] Int. Cl.$^5$ .................... A61K 39/00; A61K 37/02; C07K 7/10; C07K 7/00
[52] U.S. Cl. .................................... 424/88; 530/350; 530/324; 514/12
[58] Field of Search ............... 530/326, 325, 324, 350; 514/12; 424/88

[56] References Cited

U.S. PATENT DOCUMENTS

| | | | |
|---|---|---|---|
| 4,466,917 | 8/1987 | Nussenzweig et al. | 530/350 |
| 4,707,357 | 11/1987 | Dame et al. | 424/88 |
| 4,735,799 | 4/1988 | Patarroyo | 424/88 |
| 4,886,782 | 12/1989 | Good et al. | 424/88 |

FOREIGN PATENT DOCUMENTS 0166410  6/1986  European Pat. Off. .............. 424/88

OTHER PUBLICATIONS

Patarroyo, M. et al., Nature, 328:629–632, Aug. 13, 1987.
Trager, British Medical Bulletin, 38:129, 1982.
Nardin Nussenzweig et al., J. Exp. Med., 156:20, 1982.
Freeman and Holder, J. Exp. Med., 158:1647, 1983.
Perrin et al., J. Exp. Med., 160:441, 1984.
Perlmann et al., J. Exp. Med., 159:1686, 1984.
Collins et al., Nature, 323:259, Sep. 18, 1986.
Zavala et al., Science, 228:1436, 1985.
Holder et al., Nature, 292:361, Nov. 26, 1981.
Bitte et al., Nature, 298:30, Jul. 1, 1982.
Wahlgren et al., Clin. Exp. Immunol., 53, 127–134, 1983.
Coppel et al., Nature, 310:789, Aug. 30, 1984.
Koenen et al., Nature, 311:382, Sep. 27, 1984.
Gysin et al., J. Exp. Med., 160:935, 1984.
Perkins, J. Exp. Med., 160:788, 1984.
Cheung et al., Proc. Natl. Acad. Sci., U.S.A., 83:8328, 1986.
Bianco et al., Proc. Natl. Acad. Sci., U.S.A., 83; 8713, 1986.
Weber et al., Nucl. Acids Res., 14(8):3311–3323, 1986.
Perlmann, Parasitoloy Today, 2(5); 127–130, 1986.
Houghten, Proc. Natl. Acad. Sci., U.S.A., 82:5131, 1985.
Holder et al., Nature, 317:270, Sep. 19, 1985.
Stanley et al., J. Immunol., 134:3439, 1985.
Stanley et al., Proc. N. Acad. Sci., U.S.A., 83:6093, 1986.
Wellems et al., Proc. Natl. Acad. Sci., U.S.A., 83:6065, 1986.
Happ, T., J. of Immunological Methods, 88:1–18, 1986.
Berzofshy et al., Proc. Natl. Acad. Sci., U.S.A., 82:7048–7052, Oct. 1985.
Chou, P. et al., Am. Rev. Biochem. 47: 251–76, 1978.
Chou, P. et al., Biochemistry, 13(2); 211, 1974.
Secondary Structure Prediction by Chou and Fasman Algorithm, Intelli Genetics.
Rooman et al., Nature, 335, 45–49 (9/1/88).
Dyson et al., Ann. Rev. Biophys. Chem., 17, 305–324 (1988).
Sutcliffe et al., Protein Eng., 1, No. 5, pp. 377–384 (1987).
Kabsch et al., Proc. Natl. Acad. Sci., U.S.A., 81, 1075–78 (2/84).
Tainer et al., Nature, 312, No. 5990, 127–133 (11/8/84).
Rothbard et al., EMBO J., 7, No. 1, 93–100 (1988).
Hubbard et al., Protein Eng., 1, No. 3, 159–171 (1987).
Sternberg, Anti-Cancer Drug Design, 1, 169–178 (1986).

Primary Examiner—Howard E. Schain
Assistant Examiner—Susan M. Perkins
Attorney, Agent, or Firm—Abelman Frayne Rezac & Schwab

[57] ABSTRACT

A mixture of the synthetic peptide compounds of the formulas:

Formula (I) Tyr-Gly-Gly-Pro-Ala-Asn-Lys-Lys-Asn-Ala-Gly-OH,

Formula (II) Asp-Glu-Leu-Glu-Ala-Glu-Thr-Gln-Asn-Val-Tyr-Ala-Ala-NH$_2$, and

Formula (III) Tyr-Ser-Leu-Phe-Gln-Lys-Glu-Lys-Met-Val-Leu-NH$_2$, and compositions thereof, induces antibodies against the late stages of Plasmodium faciparum malaria and provides protection against infection with this parasite, thus providing a synthetic malaria vaccine for Plasmodium falciparum induced malaria.

A synthetic protein copolymer vaccine, polymerized from a monomer which is a hybrid of formulas (II), (III) and (I), and which also includes the (Asn-Ala-Asn-Pro) sequence of the CS protein between formulas (II) and (III) and Formulas (III) and (I) of the monomer, has been shown to provide safe and complete self-limiting protection in human volunteers against the asexual blood stages of P. faciparum induced malaria.

17 Claims, No Drawings

PROTEIN COPOLYMER MALARIA VACCINE

CROSSREFERENCE TO RELATED APPLICATIONS

This application is a continuation-in-part of copending application, Ser. No. 003,194, filed Jan. 14, 1987, now U.S. Pat. No. 4,735,799.

BACKGROUND OF THE INVENTION

This invention relates generally to the chemical synthesis of certain peptides and, more particularly, to the use of a mixture of certain of these synthesized peptides as a synthetic vaccine against malaria. This invention also relates to a synthetic hybrid protein copolymer and its use as a vaccine in humans against the asexual blood stages of *Plasmodium falciparum* induced malaria.

To eradicate malaria, which is dangerously spreading in the developing countries, where more than half of the world's susceptible population lives, scientists are looking for means to control, via chemically synthesized or genetically engineered vaccines, this deadly and threatening parasitic disease.

There are four species of human plasmodia parasites: *Plasmodium vivax; P. ovale; P. malariae* and *P. falciparum*. *P. falciparum* is the most common and lethal. When the malaria infected anopheles mosquito, bites a non-immune person it injects infectious forms of the parasite called sporozoites (first stage) living inside her salivary glands, into the host bloodstream, which within 5 minutes reaches the liver, infecting the liver cells and remains there for about one week.

Each one of these infectious particles or sporozoites divides into 20,000 to 30,000 merozoites (second stage) contained in a bag, or schizont, inside the liver cells. When the cells burst, the merozoites enter the bloodstream and invade circulating red blood cells. Inside these red blood cells (or asexual blood stage), merozoites grow, evolving through several and successive differentiation stages, namely, ring, trophozoite, schizont and merozoite, dividing and breaking out every 48 hours and producing the clinical symptoms of the disease, such as chills and fever, typical of the major forms of malaria. Each new merozoite produces 16–32 offspring that in turn infect new red blood cells, perpertuating the disease and its clinical symptoms.

After several weeks some merozoites differentiate into either male or female gametocytes (third or sexual blood stage) in the bloodstream and when another mosquito bites, it sucks up the malaria infected red blood cells containing gametocytes. Inside the female mosquito the gametocytes break out of the cells and fuse, forming a new generation of sporozoites starting the cycle once again.

A conventional vaccine using attenuated or dead malaria parasites is not feasible due to difficulties in obtaining large amounts of merozoites and contaminating red blood cell debris which potentially will create an autoimmune hemolytic anemia. In fact it was not until 1976 when William Trager developed a laboratory method to enable one to grow small amounts of *P. falciparum* blood in asexual stages (British Medical Bulletin 38:129, 1982).

The alternatives are then the development by modern techniques, such as chemical synthesis or recombinant DNA, of proteins able to induce protective immunity against the parasite infection.

In this regard, several groups have tried to identify potential targets for immunological attack of the extracellular stages of the parasite, namely, sporozoite, merozoite and gametocytes, the first two being briefly exposed in the blood circulation to the immune system.

Nussenzweig et al. (J. Exp. Med. 156:20, 1982) have identified a protein localized on the surface of sporozoites. Antibodies against this structure confer protection against the experimental disease. It is, however, generally accepted that a vaccine based only on sporozoites will not suffice to prevent malaria. Research to develop a polyvalent vaccine including merozoite and sporozoites targets is actively being pursued in many laboratories throughout the world.

Freeman and Holder (J. Exp. Med. 158:1647, 1983) have characterized a major antigen on the surface of merozoites of 195KD (kilodaltons) protein that generates, upon cleavage, proteins of 83KD, 42KD and 19KD. The first of these, the 83KD protein, remains on the surface of the merozoites. The data suggests that this antigen could be a possible target of protective immunity. Separately, Perrin et al. (J. Exp. Med. 160:441, 1984) have shown protection against blood stage induced malaria in squirrel monkeys when vaccinated with a protein of 140KD.

Perlmann et al. (J. Exp. Med. 159:1686, 1984) have recognized that 155KD protein antigen is invariably deposited on the surface of the *P. falciparum* infected red blood cells and clinical immunity in endemic areas appears to correlate with antibodies raised against certain parts of this molecule. Collins et al. (Nature 323:259, Sept. 18, 1986) have shown partial protection of Aotus trivirgatus monkeys immunized with genetically engineered fragments of this 155KD protein.

Zavala, et al., Science, 228:1436, 1985 disclose that protective immunity against *P. falciparum* can be obtained with irradiated sporozoites. The protective antigens, known as circumsporozoite proteins (CS) are polypeptides that cover the surface membrane of the parasite. The CS proteins contain species-specific immuno-dominant epitopes formed by tandem repeated sequences of amino acids. It is shown that the dominant epitope of *Plasmodium falciparum* is contained in the synthetic dodecapeptide (Asn-Ala-Asn-Pro)$_3$, or (NANP)$_3$.

SUMMARY OF THE INVENTION

It has been found that a mixture of the following chemically synthesized novel peptide compounds, having the formulas:

(I) Tyr-Gly-Gly-Pro-Ala-Asn-Lys-Lys-Asn-Ala-Gly-OH and (II) Asp-Glu-Leu-Glu-Ala-Glu-Thr-Gln-Asn-Val-Tyr-Ala-Ala-NH$_2$;

and a chemically synthesized, novel peptide compound selected from the group consisting of:

(III) Tyr-Ser-Leu-Phe-Gln-Lys-Glu-Lys-Met-Val-Leu-NH$_2$, (IV) Lys-Leu-Tyr-Gln-Ala-Gln-Tyr-Asp-Leu-Ser-Ile-OH, or (V) Lys-Lys-Phe-Thr-Lys-Asp-Glu-Asn-Lys-Pro-Asp-Glu-OH provide complete protective immunity against *P. falciparum* malaria.

When an equal mixture, weight-by-weight, of the peptide compounds of Formulas I, II and III, were injected in the form of a vaccine into the highly susceptible experimental model, the *Aotus trivirgatus* monkey, high antibody titers were induced against the peptides themselves and also reacted with the *Plasmodium falciparum* parasite by different immunological methods. The mixture of peptides of Formulas I, II and III were able to induce protective immunity in the immunized monkeys since animals vaccinated with this mixture of peptides either did not develop the disease, or else developed a mild parasitemia when injected with the lethal live, fresh *Plasmodium falciparum* parasites.

It has also now been found that a synthetic protein copolymer, which is polymerized from a monomer which comprises a hybrid of Formulas (II), (III) and (I), referred to previously, and which includes the Asn-Ala-Asn-Pro sequence, also known as (NANP), of the circumsporozoite (CS) protein, has been shown to induce complete, self-limiting protection in human volunteers, vaccinated two or three times with the synthetic protein copolymer of the present invention. These volunteers had been exposed to experimental intravenous innoculation of red blood cells infected with one million fresh live *Plasmodium falciparum* ring stage particles. This synthetic hybrid protein, which is referred to for convenience as SPf 66, provides the first safe synthetic vaccine against the asexual blood stages of human malaria. The structural formula of the monomer of the present invention from which the protein copolymer of the present invention is polymerized is induce protective immunity in the immunized human volunteers since 1 of the volunteers failed to develop the disease, 2 developed only low parasitemias and recovered spontaneously, 1 withdrew with low parasitemias, and the 5th volunteer developed the disease in a manner similar to the non-immunized control group. The foregoing, which will be presented in greater detail in the examples, provides significant evidence that the protein copolymer of the present invention is the first synthetic vaccine which has been found to be safe for human use against the asexual blood stages of *P. falciparum* induced malaria.

DETAILED DESCRIPTION OF THE INVENTION

It has been established that a mixture of the following novel peptide compounds represents a preferred embodiment of the present invention, namely, Formula (I) Tyr-Gly-Gly-Pro-Ala-Asn-Lys-Lys-Asn-Ala-Gly-OH, Formula (II) Asp-Glu-Leu-Glu-Ala-Glu-Thr-Gln-Asn-Val-Tyr-Ala-Ala-NH$_2$, and Formula (III) Tyr-Ser-Leu-Phe-Gln-Lys-Glu-Lys-Met-Val-Leu-NH$_2$, when employed in about a 1:1:1 mixture, weight-by-weight, up to about a 10:10:10 mixture, weight-by-weight, provide a synthetic vaccine which has been

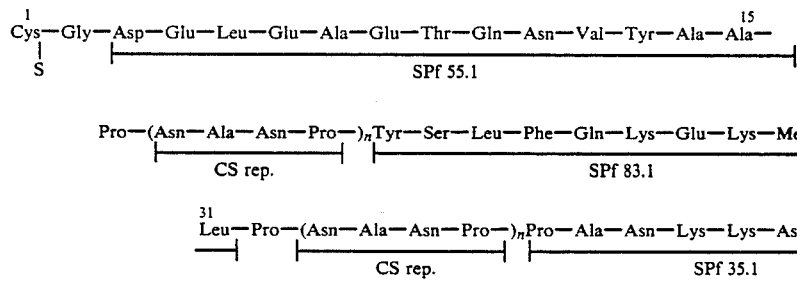

in which n is an integer from 1 to about 10.

The structural formula of the protein copolymer of the present invention is:

found to provide complete protective immunity against *P. falciparum* induced malaria.

The protein copolymer of the present invention is

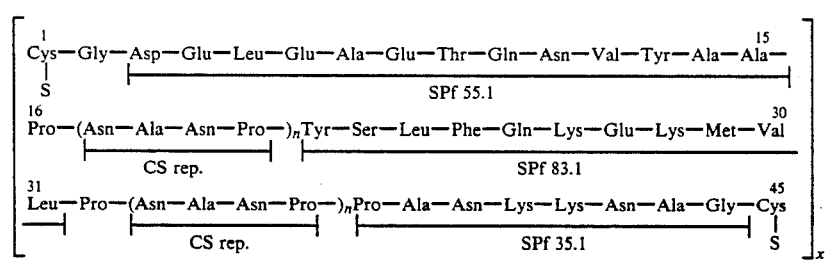

in which n is an integer from 1 to about 10 and x is an integer from 2 to about 50.

When an equal mixture, volume-to-volume, of the protein copolymer of the present invention in aluminum hydroxide was injected in the form of a vaccine to five (5) human volunteers, significant antibody titers as measured by ELISA (Enzyme Linked Immunosorbent Assay) and immunofluoresence were detected. Additionally, elevated cellular immune responses as measured by peripheral blood mononuclear cell blastogenic responses as against the protein copolymer and *P. falciparum* sonicates were identified. The synthetic hybrid protein copolymer of the present invention was able to comprised of: (1) the peptide SPf 55.1, which consists of a chain of 13 amino acids, which is the same as Formula (II) above; (2) the (Asn-Ala-Asn-Pro) epitope of the *P. falciparum* circumsporozoite protein; (3) the peptide SPf 83.1, which consists of a chain of 11 amino acids, which is the same as Formula (III) above; (4) the (Asn-Ala-Asn-Pro) epitope of the *P. falciparum* circumsporozoite protein, and (5) the peptide SPf 35.1, which consists of a chain of 8 amino acids, which is the same as Formula (I) above except for the absence Tyr-Gly-Gly at the beginning of the peptide. During the synthesis of the protein copolymer the amino acids Tyr-Gly-Gly were omitted to allow the molecule to assume an appropriate steric configuration to provide it with the same immunogenic properties possessed by the parasite. Additionally, cysteines (CS) were added at the amino and carboxy terminal ends, with Gly and Pro employed as spacers, as indicated in Formula (VII).

The molecular mass of Formula (VI) is about 5000 Daltons. When polymerized via the cysteine bridges, or bonds, it is preferred that it be polymerized to about 150 Kilodaltons, namely, about thirty (30) times its monomeric mass. While it has been found that when x equals 30 in Formula (VII) the protein copolymer has optimum stability and immunogenicity, based on the combination of solubility and size of the molecule, x can vary from 2 to about 50 without any significant sacrifice or loss in its immunogenic response.

In the (Asn-Aln-Asn-Pro)$_n$ epitope or sequence, as illustrated in Formula (VII), n can vary from 1 to about 10, with a value of 3 being preferred in that it provides an optimum immunogenic response against P. falciparum sporozoites.

The protein copolymer of the present invention when adsorbed onto aluminum hydroxide and employed to effect immunization, has proven to be immunogenic and safe for human use by various humoral and cellular tests employed to determine immunity. After intravenous challenge with 1 million live P. falciparum ring infected erythrocytes, all of the nonvaccinated human volunteers developed parasitemias which required treatment. Strikingly, three of the four subjects vaccinated with SPf(66)$_{30}$, which is the preferred polymeric protein of the present invention, developed only low parasitemias and recovered spontaneously without any treatment. One of the subjects, with low parasitemia, withdrew from the trials. In the examples which follow, additional detailed information is provided.

The novel peptide compounds of the present invention and their properties as a vaccine for P. falciparum malaria when employed in a mixture were determined in the following fashion.

As a result of my investigations, protein molecules of 155KD, 83KD, 55KD and 35KD, which are specific for the late schizont and merozoite stages of the P. falciparum parasite, were found capable of eliciting either partial or total protective immunity in Aotus monkeys immunized with the individual proteins and experimentally infected with P. falciparum parasites.

The synthesized peptide compounds of Formulas I and II are alpha hydrophilic structures, corresponding to the amino terminal parts of the molecules 35KD and 55KD, respectively, which offer in some vaccinated animals protective immunity against P. falciparum malaria in a fashion similar to the naturally occuring protein in the merozoite parasite. Each of the peptide compounds represented by Formulas I and II, even when they were employed individually, elicited antibodies and as a result delayed in some vaccinated animals the appearance of parasitemia for a period of two to five days when compared with non-immunized controls, or animals immunized with other peptide compounds.

When the peptide compounds of Formulas I and II were employed as a 1:1 mixture, weight-by-weight, 50% of the immunized animals developed mild parasitemia from which they spontaneously recovered, while the other 50% were not protected at all, suggesting that this particular mixture of peptide compounds provides partial protective immunity against P. falciparum induced malaria, rather than complete protective immunity.

The novel peptide compounds according to Formula III, IV and V were synthesized according to a specific amino acid sequence of the 195KD protein described by Holder et al. in Nature, Vol. 317, pages 270-273, Sept. 1985. Of the fifteen (15) peptides which were synthesized, most of them induced antibodies, but only the three peptides compounds, according to Formulas III, IV and V, provided partial protective immunity against P. falciparum induced malaria.

The peptide of Formula III, which corresponds to amino acid residues 43-53 of the 195KD amino acid sequence, has an alpha hydrophilic structure. The peptide of Formula IV, which corresponds to residues 277-287 of the 195KD amino acid sequence, has a random structure, while the peptide of Formula V, corresponding to residues 595-606 of the 195KD amino acid sequence, has a reverse turn structure according to the Chou Fassman method of determining the secondary structure. (Adv. Enzymol. 47:45, 1978).

The individual peptide compounds of Formulas III and V each induced a delay in the appearance of parasitemia in some animals when used for immunization against the P. falciparum induced malaria. The peptide compound of Formula IV when used individually for immunization, induced a spontaneous recovery in two of the four vaccinated animals against the P. falciparum induced malaria.

The peptide compounds of the present invention can be coupled to a carrier molecule, e.g., bovine serum albumin, by glutaraldehyde or any other coupling agent in order to induce a better immune response against the peptide due to the increased size of the molecule. Another available means for inducing a better immune response would be to copolymerize a mixture of two or three of the peptide compounds of the present invention to increase the size of the molecule.

Since the peptide compounds of the present invention are hydrophilic in nature, any mixture of the peptides can readily be prepared into an injectable form of the vaccine for parenteral administration by dissolving them in normal saline solution as the vehicle, or in an oil-based vehicle, such as, for example, squalene. Similarly, the synthesized peptide copolymer of the present invention, Formula VII, can be dissolved in saline solution, or squalene, or adsorbed to aluminum hydroxide, which is the preferred vehicle for administration to human beings by injection.

The following examples are provided to illustrate the preparation and activity of the compounds and compositions of the present invention. They are not intended to be limiting upon the scope thereof.

As employed herein, the following abbreviations shall be deemed to have the following meanings:
Boc—tertiary-butoxycarbonyl
But—tertiary-butyl (as ether-forming group)
DCC—N,N'-dicyclohexylurea
DCCI—N,N'-dicyclohexylcarbodiimide
DCM—dichloromethane
DMF—dimethylformamide
DIEA—diisopropylethyl amide
TEA—triethanolamine
TFA—trifluoroacetic acid
HF—hydrogen fluoride
Me$_2$S—dimethyl sulfide
Ala—alanine
Asn—asparagine Gln—glutamine
Glu—glutamic acid
Gly—glycine
Ile—isoleucine
Leu—leucine
Lys—lysine
Met—methionine
Phe—phenylalanine
Pro—proline
Ser—serine
Thr—threonine
Tyr—tyrosine
Val—valine

EXAMPLE 1

General Procedure for the Solid Phase Synthesis of the Peptide Compounds of the Present Invention Solid phase peptide synthesis (SPPS) is employed according to the method originally described in 1963 by M. B. Merrifield on a Beckman Peptide Synthesizer Model 990B. The method involves coupling amino acids from the carboxy terminal end to the N-terminal end of the peptide once the first amino acid is attached to an insoluble solid support.

The polystyrene resin solid support employed is a copolymer of styrene with about 1% to 2%, by weight, of divinylbenzene as a crosslinking agent which causes the polystyrene polymer to be completely insoluble in most organic solvents, but which causes it to swell extensively in DCM and DMF. This allows the penetration and free transit of solvents and reagents, thus permitting the various chemical reactions to proceed.

The solid support is made functional by the introduction of the insoluble p-methylbenzhydramine. HC1 (p-MBHA) resin having free amino groups (0.4 to 0.6 milliequivalents per gram of resin). The resin is swollen by three washes of ten minutes each with DCM with constant stirring. The acidic groups are neutralized with 5% DIEA in DCM to permit attachment of the first amino acid.

The attachment is accomplished by dissolving an excess of Boc-amino acid in 10 milliliters of DCM, or in a mixture of DCM:DMF (2:1), and is activated with 3 equivalents of DCCI in 4 milliliters of DCM. This mixture is employed to couple the first amino acid via its carboxyl group to the activated resin. To assure complete coupling, it is checked by the ninhydrin reaction.

After the first amino acid has been attached, an amino acyl resin had been formed which is used to add the other Boc-amino acids in the desired sequence via a series of steps which results in elongation of the peptide chain.

The steps are as follows:

1. Acid deprotection of the N-terminal group of the attached Boc-amino acid. Selective removal of the Boc group is accomplished with 50% TFA in DCM for 20 minutes.
2. Neutralization of excess acid with 5% DIEA in DCM.
3. Activation and Coupling of the next Boc-amino acid-A Boc-amino acid which was previously activated with DCCI is coupled to the amino acyl resin to form the peptide bond.

The excess of uncoupled amino acid is then removed by filtration and the amount of coupled Boc-amino acid is determined by the ninhydrin reaction. Then the cycle commences once again.

EXAMPLE 2

The general procedure to be followed in each synthesis cycle for each peptide utilizes 4 grams of the dried amino acyl resin, prepared in accordance Example 1 above, and employs the Beckman Peptide Synthesizer Model 990B, wherein the reagents are added stepwise, is as follows:

1. The amino acyl resin is washed four (4) times for 1 minute with 70 mls. of DCM with constant stirring. Excess reagents are removed by suction on the Synthesizer's sintered glass funnel.
2. 70 mls. of a mixture of 40 parts of TFA and 60 parts of DCM are added to the amino acyl resin two (2) times for 1 minute each with constant stirring.
3. 70 mls. of a mixture of 40 parts TFA and 60 parts DCM are added to the amino acyl resin and stirred constantly for 20 minutes.
4. 70 mls. of DCM is added to the amino acyl resin 6 times for 1 minute each with constant stirring.
5. A 70 ml. mixture of 5 parts DIEA and 95 DCM is added twice for 2 minutes with constant stirring.
6. 70 mls. of DCM is added four times for one minute each with constant stirring.
7. Protected amino acid: 3 equivalents in 15 mls. of DCM +DCCI and 3 equivalents in 5 mls of DCM are constantly stirred for 60 minutes.
8. 70 mls. of DCM is added four times for 1 minute each with constant stirring.
9. A 70 ml. mixture of 5 parts DIEA and 95 parts DCM is added while being stirred constantly for 2 minutes.
10. 70 mls. of DCM is added four times for 1 minute each with constant stirring.
11. 70 mls. of DMF is added two times for 2 minutes each with constant stirring.
12. Protected amino acid: 1 equivalent in 5 ml. of DCM at 0° C., add 0.5 equivalents of DCC at 0° C., both for 15 minutes with constant stirring, filter, wash the precipitate for 60 minutes with 15 mls. of DMF with constant stirring.
13. 70 mls. of DMF is added twice with constant stirring for a period of 2 minutes each.
14. 70 mls. of DCM is added four times with constant stirring for 1 minute.
15. Two to five mgs. of sample employed to determine free amino groups by the ninhydrin reaction.

If the result is positive, return to step 9 to perform a third coupling. If negative, a new cycle is begun. The cycles are repeated until the desired sequence is completed. The peptides are obtained by deprotection and cleavage of the obtained product with high and low concentrations of HF.

In the teflon coated reation vessel of the Beckman 990 Synthesizer, there is added 500 milligrams of the synthesized peptide resin and to it is added HF in low concentration, namely, HF/P-Cresol/Me$_2$S (25:10:65, v/v). It is incubated for 2 hours at 0° C. with constant stirring.

By vacuum suction or nitrogen flushing the HF and Me$_2$S is removed and then HF in high concentration is added, namely, HF/P-Cresol (90:10, v/v), incubate for 1 hour at 0° C. with constant stirring. The product is then washed 10 times with 5 mls. of ethyl-ether and the free peptide is extracted with 10 mls. of 5% acetic acid added 10 times.

The crude peptide fraction is analyzed by high performance liquid chromatography in octadesyl (ODS)

columns. In most instances the product is free of contaminants, but purification can be achieved, if necessary, by ion-exchange column chromatography or reverse phase liquid chromatography in ODS columns. The amino acid sequence of the peptide is reconfirmed by amino acid sequencing in an automatic Beckman 890M sequencer.

EXAMPLE 3

1 milligram of peptide prepared according to the procedure of Example 2 is coupled to 1 milligram of bovine serum albumin with 20 microliters of glutaraldehyde with constant stirring for 20 hours. The excess of peptide and glutaraldehyde is removed by dialysis against double distilled water overnight.

The coupled peptide is then lyophilized and resuspended in saline solution.

EXAMPLE 4

IMMUNIZATIONS

Groups of four (4) to six (6) Colombian Aotus trivirgatus monkeys were injected on days 0, 30, 45, 60 and 75 with 250 micrograms of each purified and coupled peptide employed in each of the peptide mixtures described hereinafter in Table 1 and the text following thereafter, namely, (a) Formulas I and II, and (b) Formulas I, II and III. Blood samples for antibody studies were taken on days 50, 70 and 80. On day 90, 15 days after the last immunization, the challenge was performed. Each monkey was intravenously inoculated with fresh blood cells infected with $5 \times 10^6$ P. falciparum parasites obtained from a donor Aotus trivirgatus monkey infected with at least 10% parasitemia of the FVO (Falciparum Vietnam Oak Knoll) strain, adapted to grow in these monkeys in which it induces a lethal disease. The controls, inoculated with saline solution, followed the same immunization pattern.

Parasitemia was monitored daily by peripheral blood smears stained with Giemsa and/or Acridine Orange Flourescence of fresh blood anticoagulated with heparine and diluted 1:1 with saline solution. Partial protection was defined as a significant delay in the appearance of the parasitemia and total protection was defined as less than 10% parasitemia which spontaneously recovered, or a complete absence of parasites in their blood.

In Table 1 the first grouping of three Aotus monkeys represents a control with the monkeys having been inoculated with only normal saline solution. The second grouping in Table 1 represents the data from eight Aotus monkeys immunized with a 1:1, weight-by-weight, mixture of the synthesized peptides of Formulas I and II of the present invention (SPf 35.1 and SPf 55.1). The third grouping in Table 1 represents the data from six Aotus monkeys immunized with a 1:1:1, weight-by-weight, mixture of the synthesized peptides of Formulas I, II and III of the present invention (SPf 35.1, SPf 55.1 and SPf 83.1).

It can be seen from the results in Table 1, that 4 of the 8 Aotus monkeys immunized with the mixture of two synthesized peptides, namely, Formulas I and II, (1:1 w/w), (SPf 35.1 and SPf 55.1) developed a disease similar to the controls, while the remaining 4 developed parasitemias lower than 10% that spontaneously recovered. In these animals, parasitemia continued to be negative until day 90, suggesting a significant protective effect provided by this mixture of two peptides.

In the same challenge, of the 6 monkeys immunized with a mixture of the three peptides, namely, Formulas I, II and III, (1:1:1 w/w), (SPf 35.1, SPf 55.1 and SPf 83.1), three of the six monkeys immunized with this mixture developed a very mild infection with parasitemia maximums of 5%, that peaked 10 to 15 days later than the control group and then spontaneously recovered. The remaining 3 Aotus trivirgatus monkeys of this same group, namely, monkeys 291, 297 and 300, did not show any signs of this disease. Furthermore, no parasites at all were detected in blood smear samples up to 90 days after the challenge.

These results show that certain combinations of the peptides synthesized, namely, a mixture of the compounds of Formulas I, II and III, according to the amino acid sequences of these molecules, which had already been shown to offer total or partial immunity against experimental infection, are capable of inducing total, sterile protection in immunized animals.

TABLE 1

| | POSTCHALLENGE PARASITEMIA IN AOTUS MONKEYS IMMUNIZED WITH SYNTHETIC PEPTIDES | | | | | | | | | | | | |
|---|---|---|---|---|---|---|---|---|---|---|---|---|---|
| | PERCENTAGE OF PARASITEMIA AFTER CHALLENGE ON DAYS | | | | | | | | | | | | |
| | Monkey Number | 4 | 5 | 6 | 7 | 8 | 9 | 10 | 11 | 12 | 13 | 14 | 15 |
| Controls | 358 | .1 | 0 | .9 | .9 | 5.3 | 7.9 | 10.2 | 28.4 | Q | | | |
| | 357 | 0 | 0 | .1 | 0 | .5 | 1.6 | 2.8 | 4.0 | 7.4 | 28.4 | Q | |
| | 359 | .1 | 0 | .5 | .9 | .9 | 2.4 | 2.5 | 5.4 | 9.0 | 9.0 | 4.5 | 11.5 |
| Mixture | 229 | 0 | 0 | .8 | .5 | 1.5 | 5.0 | 6.6 | 32.5 | Q | | | |
| of | 255 | 0 | 0 | .6 | 1.0 | 3.7 | 6.7 | 10.9 | 31.0 | Q | | | |
| SPf 35.1 | 287 | 0 | 0 | .8 | .8 | 1.0 | 1.6 | 4.1 | 6.0 | 11.8 | 9.6 | 9.8 | 10.00 |
| and | 251 | 0 | 0 | 0 | 0 | 0 | 0 | 0 | .2 | .2 | 1.2 | 3.2 | ND |
| SPf 55.1 | 275 | 0 | 0 | 0 | .1 | .5 | .5 | .5 | 2.0 | 4.0 | 6.5 | 6.0 | 6.6 |
| | 288 | 0 | 0 | 0 | .2 | .1 | 0 | 1.0 | .6 | 2.3 | ND | 4.5 | |
| | 289 | 0 | 0 | 0 | .2 | .1 | .2 | 1.0 | 2.3 | 6.4 | 10.4 | 6.8 | 2.7 |
| | 286 | 0 | 0 | .1 | 0 | .1 | .4 | .4 | 3.5 | 3.7 | 3.2 | ND | .2 |
| Mixture | 295 | 0 | 0 | 0 | 0 | 0 | 0 | 0 | 0 | 0 | 0 | | 0 |
| of | 298 | 0 | 0 | 0 | 0 | 0 | 0 | 0 | 0 | 0 | 0 | 0 | 0 |
| SPf 35.1 | 290 | 0 | 0 | 0 | .1 | 0 | 0 | 0 | .3 | 0 | .7 | .1 | .7 |
| SPf 55.1 | 291 | 0 | 0 | 0 | 0 | 0 | 0 | 0 | 0 | 0 | 0 | 0 | 0 |
| and | 297 | 0 | 0 | 0 | 0 | 0 | 0 | 0 | 0 | 0 | 0 | 0 | 0 |
| SPf 83.1 | 300 | 0 | 0 | 0 | 0 | 0 | 0 | 0 | 0 | 0 | 0 | 0 | 0 |
| | Monkey Number | 16 | 17 | 19 | 20 | 22 | 24 | 26 | 28 | 30 | 36 | 40 | 45 | 60 | 76 | 80 |
| Controls | 358 | | | | | | | | | | | | | | | |
| | 357 | | | | | | | | | | | | | | | |
| | 359 | 12.0 | 19.0 | Q | | | | | | | | | | | | |

TABLE 1-continued
POSTCHALLENGE PARASITEMIA IN AOTUS MONKEYS IMMUNIZED WITH SYNTHETIC PEPTIDES

PERCENTAGE OF PARASITEMIA AFTER CHALLENGE ON DAYS

| | | | | | | | | | | | | | | | | |
|---|---|---|---|---|---|---|---|---|---|---|---|---|---|---|---|---|
| Mixture of SPf 35.1 and SPf 55.1 | 229 | | | | | | | | | | | | | | | |
| | 255 | | | | | | | | | | | | | | | |
| | 287 | 10.5 | Q | | | | | | | | | | | | | |
| | 251 | 11.6 | Q | | | | | | | | | | | | | |
| | 275 | ND | 8.3 | .0 | .6 | .5 | .4 | .1 | 0 | 0 | 0 | 0 | 0 | 0 | 0 | 0 |
| | 288 | 5.7 | 3.1 | 1.0 | 1.0 | .5 | .1 | 0 | 0 | 0 | 0 | 0 | 0 | 0 | 0 | 0 |
| | 289 | 5.4 | ND | .2 | .2 | .2 | .1 | 0 | 0 | 0 | 0 | 0 | 0 | 0 | 0 | 0 |
| | 286 | .2 | 0 | .2 | .2 | .2 | .2 | 0 | 0 | 0 | + | | | | | |
| Mixture of SPf 35.1 SPf 55.1 and SPf 83.1 | 295 | 0 | .1 | 0 | .3 | 4.4 | 5.5 | 2.1 | .2 | 0 | 0 | 0 | 0 | 0 | 0 | 0 |
| | 298 | 0 | .3 | 1.3 | 4.8 | .9 | .4 | .1 | 0 | 0 | 0 | 0 | 0 | 0 | 0 | 0 |
| | 290 | .4 | 2.5 | 1.1 | .6 | 0 | 0 | 0 | 0 | 0 | 0 | 0 | 0 | + | | |
| | 291 | 0 | 0 | 0 | 0 | 0 | 0 | 0 | 0 | 0 | 0 | 0 | 0 | 0 | 0 | 0 |
| | 297 | 0 | 0 | 0 | 0 | 0 | 0 | 0 | 0 | 0 | 0 | 0 | 0 | 0 | 0 | 0 |
| | 300 | 0 | 0 | 0 | 0 | 0 | 0 | 0 | 0 | 0 | 0 | 0 | 0 | 0 | 0 | 0 |

Q = beginning of chloroquine therapy designed
+ = monkey died
ND = Not Determined The development of this immunity is therefore evidence for the use of these mixtures of synthetic peptides in a vaccine against *P. falciparum* induced malaria.

EXAMPLE 5

Preparation of Synthetic Protein Copolymer

To study the safety, immunogenicity and antimalarial protection afforded by the synthetic protein copolymers of the present invention in humans, a protein copolymer, SPf(66)$_{30}$, (see Formula VII generally), was polymerized from the monomer of Formula (VI) in accordance with the procedures set forth in detail in Examples 1 and 2 above.

EXAMPLE 6

Immunization of Humans With Synthetic Protein Copolymer

Nine male volunteers (ages 18–21) were selected from among one hundred and nine healthy volunteer soldiers from the Colombian Military Forces all of whom were high school graduates. They were selected on the basis of their clinical histories, the fact they were born in non-endemic malaria areas, and their clinical status based on laboratory tests, which included hematocrit, total and differential blood cell count, complete serum chemistry, urinalysis and serological tests for the presence of antibodies to hepatitis B virus and *P. falciparum*.

No incentives, such as money or promotions, were offered. All of them had normal laboratory tests and were in excellent mental and physical condition.

Based on WHO recommendations for human trials, written consents, with the understanding that volunteers were free to withdraw at any point of the investigation, were obtained after explaining in detail, (during lectures, seminars and visits to the Immunology Institute, as well as consultations with other physicians) the nature of the study, its potential risk and benefits.

Throughout the study volunteers were questioned periodically about their willingness to continue. This study was approved by medical committees of the Colombian Military Forces and the Colombian Ministry of Public Health. For challenge studies volunteers were hospitalized at the Central Military Hospital of Colombia in Bogota, with full access to all medical services and intensive care facilities and specialists. In addition, during the hospitalization period, 6 physicians, were on call at the hospital to control the patients 24 hours a day.

Blood smears from the subjects were analyzed independently three times: by the inventor and his staff, by the scientific staff of the Central Military Hospital of Colombia and by the Colombian Malaria Erradication Service (SEM). Although WHO considers malaria to be severe when the patient reaches parasitaemias about 5%, we imposed stricter criteria, namely, that vaccines that developed parasitaemias greater than 0.5% would be treated with chloroquine followed with sulphadoxine and pyrimethamine, to ensure their complete safety.

The volunteers were divided into 4 groups: (1) two volunteers (D.A. and J.C.) received three 2 mg-doses of SPf(66)$_{30}$ adsorbed to aluminum hydroxide on days 0, 60, and 80, (2) three volunteers (W.B., W.G., and L.C.) received the same protein and dose on days 0 and 60 only, (3) three controls (volunteers A.C., J.D. and C.B.) received saline solution on days 0, 20 and 45; and (4) one volunteer (J.E.) served as naive receptor for passing on the *P. falciparum* strain. The SPf(66)$_{30}$ synthetic hybrid protein copolymer and the saline solution were adsorbed to Al(OH)$_3$ prior to inoculation.

One subject vaccinated with SPf(66)$_{30}$ (D.A.) developed a general urticarial eruption five minutes after the third immunization. No hypotension or dyspnoea developed and the rash responded rapidly to treatment with hydrocortisone and adrenaline. The cause of this reaction is unknown but was attributed to problems during the dialysis of a batch of SPf(66)$_{30}$ to remove salts, Tris and DTT. This dialysis was therefore omitted form the purification protocol and the desalting performed by gel filtration.

When the subject was vaccinated 3X with another batch of SPf(66)$_{30}$ he did not develope severe, systemic or local side effects. Slight pain, local erythema and induration at the inoculation site were, however, noted in all the subjects. None of the volunteers presented fever or showed changes in the blood cell count, blood chemistry, or urinalysis on days −1, 1, 3 and 5 after each immuization. Autoimmunity tests (Rheumatoid factor, Antinuclear Antibodies, Coombs test, and antimyocardial fiber antibodies) were systematically negative.

To study the dynamics of the humoral and cellular immune responses, blood samples were taken the day before and 15 days after each immunization, and also the day prior to the challenge. In this last sample, antibody titers were determined by peptide-antipeptide ELISA using the synthetic protein molecules as antigens. No antibodies were detected against the CS repeat molecule (NANP) in any sera.

Indirect Immunofluorescence Assay (IIFA) showed that all sera contained antibodies to merozoite-schizonts in titers between 1:20 and 1:160. Also, all preimmune sera and sera from the controls and naive receptors were negative or had antibody titers below 1:20. No correlation was found between antibody levels and anti-malarial protection, but the only unprotected vaccineee with SPf(66)$_{30}$ (J.C.), showed the lowest antibody titers by all methods.

Proliferation assays of peripheral blood mononuclear cells (PBMC) using the protein hybrids and sonicates of purified schizonts as antigens showed Stimulation Indexes (S.I.) below 3.0 before the first vaccination. After each vaccination and before the challenge, the Stimulation Indexes varied from 0.61 to 35.1 but did not correlate with either antibody titers or anti-malarial protection.

The day of the challenge volunteers were intravenously inoculated with a wild P. falciparum strain, grade I chloroquine resistant and with complete sensibility to sulphadoxine and pyrimethamine, similar to most of the Colombian wild strains. The infected red blood cells were obtained from a malaria naive volunteer (EG) previously inoculated with the thawed strain, blood group O+, compatible with all the volunteer recipients and in excellent medical, clinical and laboratory condition with all serological tests negative. The inoculum given to the volunteers was one million fresh live ring infected erythrocytes diluted in approximately 4 mls of Sterile Saline Solution. Parasitaemia levels were monitored after the third day by thick and thin blood smears stained with Giemsa, Field or Acridine Orange every 12 hours, and communicated to the volunteers by the medical staff, to determine it someone wished to withdraw. Volunteers with parasitaemias about 0.5% received immediate treatment with chloroquine followed by sulphadoxine and pyrimethamine. The individual parasitaemia evolution is shown in Table 2 for a better understanding of the protective effect of the synthetic hybrid protein copolymer. During the first four days all parasitaemias were negative. Giemsa staining readings were lower than Acridine Orange.

After the 7th day of challenge, the naive receptor and the volunteers who received saline solution had parasitaemias that rose in 12 hours from very low levels to percentages greater than 1%. Chemotherapy was given immediately with rapid clinical response and without residual effects or sequelae (Table 2).

Three of the five volunteers (W.B., W.G. and L.C.) vaccinated with SPf(66)$_{30}$ had mild infections with steady decrease in parasite counts and total recovery by day 21 (Table 2). Among them, volunteer (W.B.) had a peak of parasitaemia (0.007%) on day 7 but parasites were never seen in his blood again. The other two (W.G. and L.C.) developed parasitaemias below 0.5% that were self-limited by days 18 and 20 post-challenge. Although asexual blood forms had disappeared, a few gametocytes (average 0.04%) were still present. Since extremely few (less than 0.004%) asexual blood forms were seen in their blood some days and other were completely negative, it was decided to give them prophylactic chemotherapy by day 35. By day 40 no gametocytes or asexual blood forms were present and the volunteers' clinical conditions and clinical laboratory results were excellent. The fourth volunteer (D.A.) decided to quit the study on day 10 after having parasitaemias below 0.45% and then received prompt chemotherapy. The fifth (J.C.) developed parasitaemia similar to the control group. (Table 2).

Clinical malaria symptoms (fever, headache, nausea, etc.) were present in all volunteers infected with the parasite. Interestingly, the symptoms appeared sooner in the protected individuals than in the controls and naive receptors (day 6). Minor clinical laboratory changes attributable to malaria were observed in all the volunteers but returned to normal levels after chemotherapy.

TABLE 2

DEVELOPMENT OF POSTCHALLENGE PARASITAEMIA IN THE VACCINATED VOLUNTEERS
Percentage of parasitaemia on days after challenge

| | 5 | | 6 | | 7 | | 8 | | 9 | | 10 | | 11 | |
|---|---|---|---|---|---|---|---|---|---|---|---|---|---|---|
| | AM | PM | AM | PM | AM | PM | AM | PM | AM | PM | AM | PM | AM | PM |
| Volunteers Vaccinated with SPF(66)30 | | | | | | | | | | | | | | |
| W.B. | 0 | 0 | 0 | 0 | .002 | .007 | 0 | 0 | 0 | 0 | 0 | 0 | 0 | 0 |
| W.G. | .015 | .036 | .040 | .002 | .440 | .289 | .020 | 0 | .171 | .368 | .019 | .006 | .190 | .120 |
| L.C. | 0 | .034 | .008 | 0 | .052 | .142 | .030 | .002 | .214 | .465 | .011 | .006 | .051 | .175 |
| D.A. | .006 | .010 | .028 | .011 | .410 | .400 | .066 | .007 | .288 | 0 | .014 | Q | | |
| J.C. | 0 | .006 | .007 | 0 | .002 | .171 | .183 | .002 | .078 | 2.150 | Q | | | |
| Controls Volunteers | | | | | | | | | | | | | | |
| A.C. | 0 | .032 | .022 | .007 | .016 | 270 | 150 | 0 | .115 | 1.600 | Q | | | |
| J.D. | 0 | .033 | .026 | .005 | .008 | .870 | .780 | .017 | 4.260 | Q | | | | |
| C.B. | 0 | .120 | .072 | 0 | .300 | 2.300 | Q | | | | | | | |
| J.E. | .008 | .100 | .115 | .010 | 1.700 | 3.600 | Q | | | | | | | |

| | 12 | | 13 | | 14 | | | | | | | | |
|---|---|---|---|---|---|---|---|---|---|---|---|---|---|
| | AM | PM | AM | PM | AM | PM | 15 | 16 | 17 | 18 | 19 | 20 | 21 |
| Volunteers Vaccinated with SPF(66)30 | | | | | | | | | | | | | |
| W.B. | 0 | 0 | 0 | 0 | 0 | 0 | 0 | 0 | 0 | 0 | 0 | 0 | 0 |
| W.G. | .015 | .166 | .292 | .094 | .075 | .072 | .001 | 0 | .020 | .030 | 0 | .020 | 0 |
| L.C. | .130 | .013 | .120 | .242 | .060 | ND | .02 | .116 | .064 | 0 | 0 | 0 | 0 |

Q - Beginning of chloroquine therapy
ND - Not determined

From the experimental results set forth in Table 2 it can be seen that the synthetic protein copolymer of the present invention when used for human immunization is safe, induces significant antibody titers and high cellular immune responses against P. falciparum asexual blood stage forms. When challenge was performed in human volunteers there was produced complete, self-limiting protection against experimental infection with the asexual blood stages of the *P. falciparum* parasite, which is the first synthetic vaccine against the asexual stages of any human malaria.

The terms and expressions which have been employed are used as terms of description and not of limitation, and there is no intention in the use of such terms and expressions of excluding any equivalents of the features shown and described or any portions thereof, but it is recognized that various modifications are possible within the scope of the invention as claimed.

What is claimed is:

1. A compound of the formula

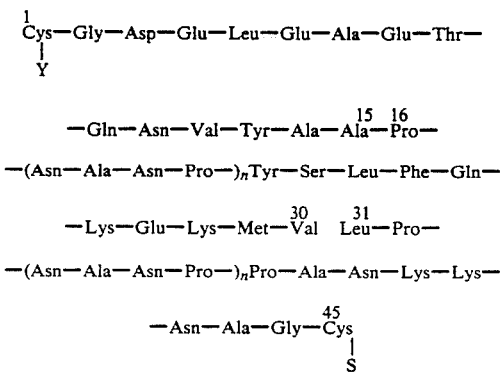

in which n is an integer from 1 to about 10.

2. A polymeric compound of the formula $$\begin{bmatrix}
\overset{1}{\text{Cys}}-\text{Gly}-\text{Asp}-\text{Glu}-\text{Leu}-\text{Glu}-\text{Ala}-\text{Glu}-\text{Thr}- \\
| \\
Y \qquad\qquad\qquad\qquad\qquad\qquad 15\ 16 \\
-\text{Gln}-\text{Asn}-\text{Val}-\text{Tyr}-\text{Ala}-\text{Ala}-\text{Pro}- \\
-(\text{Asn}-\text{Ala}-\text{Asn}-\text{Pro}-)_n\text{Tyr}-\text{Ser}-\text{Leu}-\text{Phe}-\text{Gln}- \\
\qquad\qquad\qquad\qquad 30\quad 31 \\
-\text{Lys}-\text{Glu}-\text{Lys}-\text{Met}-\text{Val}\ \text{Leu}-\text{Pro}- \\
-(\text{Asn}-\text{Ala}-\text{Asn}-\text{Pro}-)_n\text{Pro}-\text{Ala}-\text{Asn}-\text{Lys}-\text{Lys}- \\
\qquad\qquad\qquad 45 \\
-\text{Asn}-\text{Ala}-\text{Gly}-\text{Cys} \\
| \\
S
\end{bmatrix}_x$$

in which n is an integer from 1 to about 10 and x is an integer from 2 to about 50.

3. A composition for immunization against *Plasmodium falciparum* induced malaria which comprises as active ingredient the compound of claim 2 in a vehicle suitable for human administration.

4. The composition of claim 3 in which the vehicle is suitable for parenteral administration to humans.

5. A method of inducing protective immunity against *Plasmodium falciparum* induced malaria which comprises administering an immunity inducing effective amount of the composition of claim 3.

6. The method of claim 5 wherein the composition is administered by injection.

7. The compound of claim 2 wherein x is 30.

8. The compound of claim 2 wherein n is 3.

9. The composition of claim 3 wherein x is 30.

10. The composition of claim 3 wherein n is 3.

11. The method of claim 5 wherein x is 30.

12. The method of claim 5 wherein n is 3.

13. The composition of claim 4 wherein the vehicle is aluminum hydroxide.

14. The method of claim 6 wherein the vehicle is aluminum hydroxide.

15. A compound of the formula

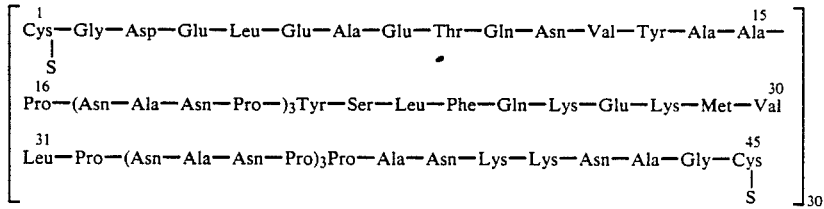

16. A composition for immunizing against *Plasmodium falciparum* induced malaria which comprises as active ingredient the compound of claim 15 in a vehicle suitable for parenteral administration.

17. A method of inducing protective immunity against *Plasmodium falciparum* induced malaria which comprises administering an immunity-inducing effective amount of the composition of claim 16.

* * * * *

UNITED STATES PATENT AND TRADEMARK OFFICE
CERTIFICATE OF CORRECTION

PATENT NO. : 4,957,738

DATED : September 18, 1990

INVENTOR(S) : Manuel E. Patarroyo

It is certified that error appears in the above-identified patent and that said Letters Patent is hereby corrected as shown below:

Claim 1, col. 15, line 19 and claim 2, col. 16, line 5, delete "Y", insert -- S --.

Signed and Sealed this

Second Day of April, 1991

Attest:

HARRY F. MANBECK, JR.

*Attesting Officer*  *Commissioner of Patents and Trademarks*